US006482771B2

(12) United States Patent
Jones

(10) Patent No.: US 6,482,771 B2
(45) Date of Patent: Nov. 19, 2002

(54) SYNERGISTIC HERBICIDAL METHODS AND COMPOSITIONS

(75) Inventor: Steven Marke Jones, Brooklyn (AU)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/818,887

(22) Filed: Mar. 27, 2001

(65) Prior Publication Data

US 2002/0002113 A1 Jan. 3, 2002

Related U.S. Application Data

(60) Provisional application No. 60/192,293, filed on Mar. 27, 2000.

(51) Int. Cl.$^7$ .......................... A01N 43/50; A01N 39/04
(52) U.S. Cl. ....................................... 504/139
(58) Field of Search .......................... 504/139

(56) References Cited

U.S. PATENT DOCUMENTS

| 5,461,019 A | 10/1995 | Willms et al. | 504/130 |
|---|---|---|---|
| 5,696,051 A | 12/1997 | Willms et al. | 504/130 |
| 5,739,080 A | 4/1998 | Boyles et al. | 504/110 |
| 6,054,410 A | * 4/2000 | Landes et al. | 504/134 |

FOREIGN PATENT DOCUMENTS

| CA | 2 327 732 | 3/1999 |
|---|---|---|
| EP | 749 688 | 12/1996 |
| WO | WO 00/08936 | 2/2000 |
| WO | WO 00/08940 | 2/2000 |

OTHER PUBLICATIONS

Hollaway et al., 1996 Weed Research, vol. 36, pp. 369–374.
XP–002177497, Chemical Abstract, *Pesticide Manual*, Tomlin et al., pp. 271–274.
XP–002177498, Chemical Abstract, *Crop Prot.*, vol. 8, No. 6, 1989 pp. 447–450.
XP–002177499, Chemical Abstract, *Weed Science*, vol. 39, 1986, pp. 158–159.
XP–002177500, Chemical Abstract, *Weed Research*, vol. 34, No. 4, 1994, pp. 251–263.
XP–002177501, Chemical Abstract, *J. Plant Growth Regul.*, vol. 16, No. 2, 1987, pp. 63–67.
XP–002177502, Chemical Abstract, *Indian J. Pharm. Sci.*, vol., 57, No. 3, 1995, pp.275–281.
XP–002177503, Chemical Abstract, *Weed Research*, vol. 35, No. 3, 1995, pp. 149–155.
XP–002177504, Chemical Abstract, *Weed Technology*, vol. 4, No. 1, 1990, pp. 169–172.

* cited by examiner

*Primary Examiner*—S. Mark Clardy
(74) *Attorney, Agent, or Firm*—Keil & Weinkauf

(57) ABSTRACT

The present invention provides a method for synergistic broad spectrum weed control which comprises applying to the weeds or their locus a synergistically effective amount of a combination of an imidazolinone herbicide plus (4-chloro-2-methylphenoxy)acetic acid (MCPA). Further provided are synergistic herbicidal compositions comprising an imidazolinone herbicide plus MCPA.

16 Claims, No Drawings

SYNERGISTIC HERBICIDAL METHODS AND COMPOSITIONS

This application claims priority from copending provisional application(s) Ser. No. 60/192,293 filed on Mar. 27, 2000.

BACKGROUND OF THE INVENTION

Imidazolinone compounds, for instance, those described in U.S. Pat. No. 4,188,487, U.S. Pat. No. 4,798,619 and U.S. Pat. No. 5,334,576, are highly potent, broad spectrum, environmentally benign, herbicidal agents. Although said imidazolinones demonstrate excellent herbicidal activity, when used as the sole active ingredient they do not always achieve effective control of the full spectrum of weed species encountered in commercial agronomic practice. Such gaps in the spectrum of control can often be remedied by co-treatment with another herbicide known to be effective against the relevant weed species. For imidazolinone resistant or tolerant crops, efficacy over a broad spectrum of weed species remain a challenge. Accordingly, there is ongoing research to create more effective imidazolinone-based broad spectrum herbicidal combinations for said crops.

Combinations of AHAS-inhibiting herbicides plus growth regulator herbicides are described in U.S. Pat. No. 5,739,080. However, U.S. Pat. No. 5,739,080 discloses the use of said combination in a method for the reduction of phytotoxicity to crop plants, particularly grass crop plants such as sorghum, corn and wheat. Although reduction in plant injury is exemplified for the combination of an AHAS-inhibiting herbicide such as a sulfonyl urea plus a growth regulator herbicide such as the benzoic acid type (e.g., dicamba) or the phenoxy acid type (e.g., 2,4-D and MCPA), no biological interaction such as antagonism or synergism is demonstrated for the combination of an imidazolinone herbicide plus MCPA. Further, no indication or anticipation of synergism is disclosed.

Therefore, it is an object of this invention to provide a method for the synergistic control of a broad spectrum of undesirable broadleaf and grass plant species.

It is another object of this invention to provide a synergistic herbicidal composition useful for broad spectrum weed control.

It is a feature of this invention that the inventive synergistic herbicidal methods and compositions may be applied in the presence of imidazolinone-resistant or imidazolinone-tolerant crops.

SUMMARY OF THE INVENTION

The present invention provides a method for the synergistic control of undesirable plants which comprises applying to the locus of said plants or to the foliage or stems of said plants a synergistically effective amount of a combination of an imidazolinone herbicide plus (4-chloro-1-methylphenoxy)acetic acid (MCPA).

The present invention also provides a synergistic herbicidal composition which comprises an agriculturally acceptable carrier and a synergistically effective amount of a combination of an imidazolinone herbicide plus MCPA.

DETAILED DESCRIPTION OF THE INVENTION

Imidazolinone compounds such as those described in U.S. Pat. No. 4,188,487; U.S. Pat. No. 4,798,619 or U.S. Pat. No. 5,334,576, are highly potent, broad spectrum, environmentally benign, herbicidal agents. Although said imidazolinones demonstrate excellent herbicidal activity when used as the sole active ingredient, they do not always achieve effective control of the full spectrum of weed species encountered in commercial agronomic practice. The widespread use of broadleaf herbicides in small grain crops has led to a shift in weed species so that effective control of grass weeds has become a significant problem in agronomic practice. Effective control of both broadleaf and grass weed species with a single herbicide typically requires high use rates and multiple applications, a practice which commonly leads to weed resistance.

Surprisingly, it has now been found that a combination which comprises an imidazolinone herbicide plus (4-chloro-2-methylphenoxy)acetic acid, (MCPA) demonstrates synergistic control of a broad spectrum of undesirable broadleaf and grass plant species. That is, the application of the combination of the invention gives a mutual reinforcing action such that the application rates of the individual herbicidal components can be reduced and still the same herbicidal effect is achieved or, alternatively, the application of the combination of herbicidal components demonstrates a greater herbicidal effect than that which can be expected from the effect of the application of the individual herbicidal components when applied singly at the rate at which they are present in the combination (synergistic effect), The combination of this invention is particularly suited for use in imidazolinone-resistant or imidazolinone-tolerant crops, preferably a cereal crop, more preferably wheat.

Imidazolinone herbicides suitable for use in the combination of the invention include compounds of formula I

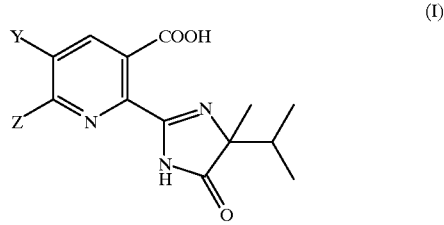

(I)

wherein
Y and Z are each independently H, $C_1$–$C_4$alkyl optionally substituted with one $C_1$–$C_4$alkoxy group or Y and Z may be taken together to form a group —CH=CH—CH=CH—.

Preferred imidazolinone compounds of formula I are:
2-(4-isopropyl-4-methyl-5-oxo-2-imidazolin-2-yl) nicotinic acid (imazapyr);
2-(4-isopropyl-4-methyl-5-oxo-2-imidazolin-2-yl)-3-quinolincarboxylic acid (imazaquin);
2-(4-isopropyl-4-methyl-5-oxo-2-imidazolin-2-yl)-5-methylnicotinic acid (imazapic;
5-ethyl-2-(4-isopropyl-4-methyl-5-oxo-2-imidazolin-2-yl)nicotinic acid (imazothapyr): or
2-(4-isopropyl-4-methyl-5-oxo-2-imidazolin-2-yl)-5-methoxymethyl)nicotinic acid (imazamox).

More preferred compounds of formula I are:
2-(4-isopropyl-4-methyl-5-oxo-2-imidazolin-2-yl)-5-(methoxymethyl)-nicotinic acid (imazamox);
2-(4-isopropyl-4-methyl-5-oxo-2-imidazolin-2-yl)-5-methyinicotinic acid (imazapic);
2-(4-isopropyl-4-methyl-5-oxo-2-imidazolin-2-yl) nicotinic acid (imazapyr); or a mixture thereof.

Especially preferred compounds of formula I are:

2-(4-isopropyl-4-methyl-5-oxo-2-imidazolin-2-yl)-5-(methoxymethyl)-nicotinic acid (imazamox);

2-(4-isopropyl-4-methyl-5-oxo-2-imidazolin-2-yl)-5-methyinicotinic acid (imazapic);

or a mixture thereof.

In the specification and claims, the term MCPA designates the auxin-type herbicide, (4-chloro-2-methylphenoxy)acetic acid, as well as its salts, alkyl or aryl amides, alkylesters, and/or alkyl thioesters. Preferably, MCPA designates (4-chloro-2-methyl-phenoxy)acetic acid, its sodium, potassium, or dimethylamine salt, its amide, t-chloroanilide, $C_1$ to $C_{10}$-alkyl ester and/or $C_1$ to $C_4$-alkylthio ester. More preferably, MCPA designates (4-chloroz-2-methylphenoxy)acetic acid, its sodium, potassium or dimethylamine salts, its amide, 2-chloroanilide, isobutyl ester, isooctyl ester and/or ethyl thioester. Most preferably, MCPA designate (4-chloro-2-methylphenoxy)acetic acid and/or its isooctyl ester.

(4-Chloro-2-methylphenoxy)acetic acid, its sodium, potassium, or dimethylamine salts, its amide, 2-chloroanilide, isobutyl ester, isooctyl ester and ethyl thioester are herbicides known from Farm Chemical Handbood '99, Meister Publishing Company 1999, p. Ci 246, C246, and Ci 303.

The synergistic herbicidal combination of the invention comprises an imidazolinone herbicide, preferably an imidazolinone of formula I, more preferably imazamox, imazapic, imazapyr, or a mixture thereof plus MCPA. Synergistic herbicidal combinations suitable for use in the method of the invention include those wherein the weight/weight ratio of imidazolinone to MCPA is about 1:4 to 1:20, especially about 1:10 to 1:20.

Thus, in accordance with the method of invention a synergistically effective amount of a combination of an imidazolinone herbicide plus MCPA is applied to the locus, foliage or stems of undesirable plants, optionally in the presence of an imidazolinone-resistant or imidazolinone-tolerant crop, preferably a cereal crop, more preferably wheat.

In actual practice, the combination of the invention may be applied to the plant stem or foliage or the locus thereof in the form of an aqueous concentrate, or water dispersible granule, a wettable powder, a soluble granule, or in any form conventionally used in agronomic practice.

The present invention also provides a synergistic herbicidal composition which comprises an agriculturally acceptable carrier and a synergistically effective amount of a combination of an imidazolinone herbicide plus MCPA. The agriculturally acceptable carrier may be a solid or a liquid, preferably a liquid, more preferably water. While not required, the synergistic herbicidal composition of the invention may also contain other additives such as fertilizers, inert formulation aids, i.e. surfactants, emulsifiers, defoamers, dyes, extenders or any of the conventional inert ingredients typically employed in herbicidal formulated products.

Imidazolinone herbicides suitable for use in the composition of the invention include compounds of formula I

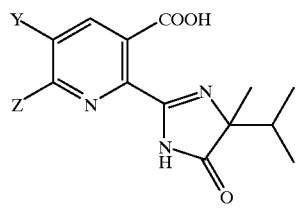

(I)

wherein

Y and Z are each independently H, $C_1$–$C_4$alkyl optionally substituted with one $C_1$–$C_4$alkoxy group or Y and Z may be taken together to form a group —CH═CH—CH═CH—.

Preferred synergistic herbicidal compositions of the invention are those compositions wherein the imidazolinone herbicide is imazamox, imazapic, imazapyr, imazethapyr, imazaquin or a mixture thereof. More preferred compositions of the present invention are those wherein the imidazolinone herbicide is imazamox, imazapic, imazapyr or a mixture thereof. Especially preferred compositions of the invention are those wherein the imidazolinone herbicide is imazamox or imazapic or a mixture thereof.

The synergistically effective amount of the combination suitable for use in the composition of the invention may vary according to prevailing conditions such as weed pressure, application timing, mode of application, weather, soil conditions, topographical character, target crop species and the like. In actual practice, application rates sufficient to provide about 0.10 kg/ha to 1.00 kg/ha, preferably about 0.25 kg/ha to 0.75 kg/ha of active ingredients are suitable.

In another embodiment of the present invention the application rate of the imidazolinone herbicide or mixture thereof is in the range of 1–200 g/ha, preferred 10–150 g/ha, more preferred 15–50 g/ha.

In another embodiment of the present invention the application rate of MCPA is in the range of 50–950 g/ha, more preferred 150–700 g/ha, especially preferred 200–400 g/ha.

For a more clear understanding of the invention, specific examples thereof are set forth below. These examples are merely illustrative, and are not to be understood as limiting the scope and underlying principles of the invention in any way.

In the following examples, synergism is determined by the Colby (Colby, S. R., Weeds, 1967(15), p. 20–22) method, i.e. the expected (or predicted) response of the combination is calculated by taking the product of the observed response for each individual component of the combination when applied alone divided by 100 and subtracting this value from the sum of the observed response for each component when applied alone. Synergism of the combination is then determined by comparing the observed response of the combination to the expected (or predicted) response as calculated from the observed responses of each individual component alone. If the observed response of the combination is greater than the expected (or predicted) response then the combination is said to be synergistic.

The foregoing is illustrated mathematically herein below, wherein a two-way combination, C, is composed of component X plus component Y and Obs. designates the observed response of the combination C.

$$(X + Y) - \frac{XY}{100} = \text{Expected response (Exp.)}$$

EXAMPLE 1

Evaluation of a Combination of an Imidazolinone Herbicide plus MCPA for Synergistic Biomass Reduction and Seedhead Suppression in *Hordeum leporinum* (Wild barley)

All trials employ standard accepted weed science procedures. Applications are made to 2×10M plots with a propane gas-powered small plot boomspray applicator. Test design is a modified randomized complete block design with four replications. Applications are made at 2–6 weeks after the imidazolinone-tolerant crop is sown.

In this evaluation biomass reduction is determined by visually rating the numbers and bulk of *Hordeum leporinum* in the treatment plots as compared to the numbers and bulk in the untreated plots. Seedhead suppression is measured by counting the seedheads of *Hordeum leporinum* in each of the treated plots and comparing to the number of seedheads in the untreated plot.

The test solutions are prepared by tank-mixing commercial formulations. All treatments also contain 0.5% v/v of an ethoxylated vegetable oil.

The treated plots are examined at intervals during the growing season and rated for percent biomass reduction and percent seedhead suppression. The data shown are an average of the replicates for that treatment. The Colby method of analysis is used to determine the resultant biological effect of the combination treatment as compared to the biological effect of each component when applied alone. The data are reported in Table I.

As can be seen from the data shown in Table I, application of the combination of imazamox plus MCPA or imazapic plus MCPA gives significantly greater biomass reduction and seedhead suppression in the grass *Hordeum leporinum* than that which could be predicted from the biomass reduction and seedhead reduction resulting from the application of either imazamox alone, imazapic alone, or MCPA alone.

TABLE I

Evaluation of Imidazolinone/MCPA Mixtures for
Biomass Reduction and Seed Head Suppression in *Hordeum leporinum*

| TREATMENT (Rate) | Bio. Red. Observed (%) | Bio. Red. Expected (%) | Seed Head Red. Observed (%) | Seed Head Red. Expected (%) |
|---|---|---|---|---|
| imazamox[1] (28 g/ha) | 80 | — | 76.33 | — |
| imazamox + MCPA LVE[2] (28 g/ha + 375 g/ha) | 95 | 80 | 95.40 | 72.12 |
| imazapic[3] (28 g/ha) | 30 | — | 5.55 | — |
| imazapic + MCPA LVE (28 g/ha + 375 g/ha) | 60 | 30 | 32.95 | −10.38 |
| MCPA LVE (375 g/ha) | 0 | — | −16.20 | — |

[1]RAPTOR ® 700 DG, manufactured by American Cyanamid Co.

TABLE I-continued

Evaluation of Imidazolinone/MCPA Mixtures for
Biomass Reduction and Seed Head Suppression in *Hordeum leporinum*

| TREATMENT (Rate) | Bio. Red. Observed (%) | Bio. Red. Expected (%) | Seed Head Red. Observed (%) | Seed Head Red. Expected (%) |
|---|---|---|---|---|

[2]MCPA LVE ®, manufactured by Nufarm UK
[3]FLAME ® 700 DG, manufactured by American Cyanamid Co.

EXAMPLE 2

Evaluation of a Combination of an Imidazolinone Herbicide Plus MCPA for Synergistic Density Reduction in *Bromus diandrus* (Great bromegrass)

Using essentially the same procedure and test solutions described in Example 1, the following evaluation is carried out. In this evaluation, density reduction is measured by counting the *Bromus diandrus* weeds in the treated plots and comparing the count to that of the untreated plot.

Treated plots are examined at intervals during the growing season and rated for percent density reduction. The Colby method of analysis is used to determine the resultant biological effect. The data are averaged and shown in Table II.

As can be seen from the data shown in Table II application of a combination of imazapic plus MCPA gave significantly greater density reduction in the grass *Bromus diandrus* than that which could be predicted from the density reduction resulting from the application of either imazapic alone or MCPA alone.

TABLE II

Evaluation of Imidazolinone/MCPA Mixtures for
Density Reduction in *Bromus diandrus*

| TREATMENT (Rate) | Density Red. Obs. (%) | Density Red. Exp. (%) |
|---|---|---|
| imazamox[1] (28 g/ha) | 98.96 | — |
| imazamox + MCPA[2] (28 g/ha + 375 g/ha) | 100 | 99.02 |
| imazapic[3] (28 g/ha) | −17.29 | — |
| imazapic + MCPA (28 g/ha + 375 g/ha) | 84.58 | 14.62 |
| MCPA (375 g/ha) | 28.78 | — |

[1]RAPTOR ® 700 DG, manufactured by American Cyanamid Co.
[2]MCPA LVE ®, manufactured by Nufarm UK
[3]FLAME ® 700 DG, manufactured by American Cyanamid Co.

What is claimed is:

1. A method for the synergistic control of undesirable plants which comprises applying to the locus of said plants or to the foliage or stems of said plants a synergistically effective amount of a combination of an imidazolinone herbicide plus MCPA.

2. The method according to claim 1 having an imidazolinone herbicide of formula I

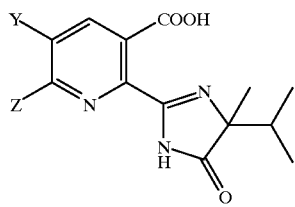

(I)

wherein
Y and Z are each independently H, $C_1$–$C_4$alkyl optionally substituted with one $C_1$–$C_4$alkoxy group or Y and Z may be taken together to form a group —CH═CH—CH═CH—.

3. The method according to claim 2 wherein the imidazolinone herbicide is imazamox, imazapyr, imazapic, imazethapyr, imazaquin or a mixture thereof.

4. The method according to claim 3 wherein said herbicide is imazamox, imazapic or imazapyr or a mixture thereof.

5. The method according to claim 3 wherein said herbicide is imazamox or imazapic or a mixture thereof.

6. The method according to claim 1 wherein the wt/wt ratio of the imidazolinone herbicide to MCPA is about 1:4 to 1:20.

7. The method according to claim 1 wherein the combination is applied in the presence of an imidazolinone-resistant or imidazolinone-tolerant crop plant, crop seed or other crop-propagating organ.

8. The method according to claim 7 wherein said crop is a cereal crop.

9. The method according to claim 8 wherein said crop is wheat.

10. A synergistic herbicidal composition which comprises an agriculturally acceptable carrier and a synergistically effective amount of a combination of an imidazolinone herbicide plus MCPA.

11. The composition according to claim 10 wherein the imidazolinone herbicide is imazamox, imazapic, imazapyr, imazethapyr, imazaquin or a mixture thereof.

12. The composition according to claim 11 wherein said herbicide is imazamox, imazapic, imazapyr or a mixture thereof.

13. The composition according to claim 11 wherein said herbicide is imazamox or imazapic or a mixture thereof.

14. The composition according to claim 10 wherein the wt/wt ratio of imidazolinone herbicide MCPA is about 1:4 to 1:20.

15. The composition according to claim 14 wherein the synergistically effective amount is an amount sufficient to supply about 0.10 kg/ha to about 1.00 kg/ha.

16. The composition according to claim 15 wherein the synergistically effective amount is sufficient to supply about 0.25 kg/ha to 0.75 kg/ha.

* * * * *